United States Patent [19]

Illingworth

[11] 4,180,691

[45] Dec. 25, 1979

[54] ALKYLATION OF AROMATIC HYDROCARBONS FOR DETERGENT PRECURSORS

[75] Inventor: George E. Illingworth, Arlington Heights, Ill.

[73] Assignee: UOP Inc., Des Plaines, Ill.

[21] Appl. No.: 931,048

[22] Filed: Aug. 4, 1978

[51] Int. Cl.$^2$ .............................................. C07C 3/54
[52] U.S. Cl. .................................................. 585/455
[58] Field of Search ........... 260/671 R, 671 B, 671 C, 260/683 R, 61, 57

[56] References Cited

U.S. PATENT DOCUMENTS

| | | | |
|---|---|---|---|
| 2,430,673 | 11/1947 | Gibson et al. ..................... | 260/671 C |
| 3,248,443 | 4/1966 | McEwan et al. ................. | 260/671 B |
| 3,369,053 | 2/1968 | Scarcello et al. ................ | 260/671 R |
| 3,795,712 | 3/1974 | Torck et al. ..................... | 260/671 B |

*Primary Examiner*—C. Davis
*Attorney, Agent, or Firm*—James R. Hoatson, Jr.; John F. Spears, Jr.; William H. Page II

[57] ABSTRACT

An improved process for the acid-catalyzed alkylation of $C_6$ to $C_9$ aromatic hydrocarbons with olefins to produce linear alkylaromatic hydrocarbons useful as detergent precursors. The alkylation reaction is performed in the presence of a surfactant to reduce the 2-phenyl isomer content of the product linear alkylaromatic hydrocarbons.

5 Claims, No Drawings

ALKYLATION OF AROMATIC HYDROCARBONS FOR DETERGENT PRECURSORS

FIELD OF THE INVENTION

The invention relates to a hydrocarbon alkylation process. The invention more specifically relates to an improvement in a process for the alkylation of aromatic carbon compounds by the introduction of an acyclic side chain using an acid catalyst such as hydrogen fluoride. It is directly concerned with a process for the production of linear alkylbenzenes for use in detergent manufacture by the reaction of mono-olefins and benzene.

PRIOR ART

The alkylation of benzene using hydrogen fluoride as a catalyst is a well established commercial process. Various aspects of the use of this process to produce detergent alkylates are described in U.S. Pat. Nos. 3,426,092; 3,484,498; 3,494,971 (all Cl. 260-471); 3,501,543 (Cl. 260-674); 3,830,865 (Cl. 260-671R) and 3,950,448 (Cl. 260-671B).

It has been recognized that the quality of a detergent is adversely effected by an increase in the 2-phenyl isomer content of the detergent alkylate used as the detergent precursor. This problem is discussed in U.S. Pat. Nos. 3,342,888; 3,387,056 and 3,509,225 (all Cl. 260-671) and 3,483,262 (Cl. 260-624).

BRIEF SUMMARY OF THE INVENTION

The invention provides an improved process for the production of detergent alkylate by the acid-catalyzed alkylation of an aromatic hydrocarbon with an olefin in the presence of a surfactant. One embodiment of the invention may be characterized as comprising the steps of contacting a $C_6$ to $C_9$ aromatic hydrocarbon, an olefin, an acid catalyst and a surfactant in a reaction zone maintained at alkylation-promoting conditions; transferring the reaction zone effluent stream comprising the catalyst, the $C_6$ to $C_9$ aromatic hydrocarbon, and an alkylaromatic hydrocarbon from the reaction zone to a phase separation zone and recovering the product alkylaromatic hydrocarbon from a hydrocarbon liquid phase formed in the phase separation zone.

DETAILED DESCRIPTION

One of the more important acid-catalyzed alkylation reactions is the production of alkylaromatic hydrocarbons commonly referred to as "detergent alkylate." This name is applied to an alkylation reaction product when it is utilized as the precursor for detergents. Detergent alkylate is often produced by the reaction of an aromatic hydrocarbon, preferably benzene, with an olefinic hydrocarbon having from 7 to 20 carbon atoms per molecule. The resulting crude detergent alkylate is then transformed into the product detergent by the sequential steps of sulfonation and neutralization.

The properties of the detergents produced in this manner are influenced by the structure of the olefinic hydrocarbon which is consumed in the alkylation reaction. For instance, a better quality detergent normally results from the use of olefinic hydrocarbons having from about 10 to 15 carbon atoms per molecule. The structure of the olefinic hydrocarbon also influences the biodegradability of the product detergent. Hard detergents result from the use of branched chain olefins such as propylene tetramer produced in a catalytic condensation process. Soft detergents are the result of using straight-chain mono-olefins as the olefinic reactant. The use of soft detergents is becoming more widespread, and the subject invention is therefore primarily directed to the production of detergent alkylates useful in the production of soft or biodegradable detergents.

It is known in the art that sulfonates of alkylaromatics and ethoxylated alkylphenols prepared from straight-chain alkenes have different detergent properties depending on the point along the length of the olefinic molecule at which it is joined to the aromatic hydrocarbon. More specifically, it is known that the attachment of the aromatic hydrocarbon to the second carbon of the alkyl chain derived from the olefinic hydrocarbon produces alkylaromatic and alkylphenyl detergent precursors which lead to a lower-quality detergent. These undesirable alkylation products are referred to as the 2-phenyl isomer of the alkylaromatic hydrocarbon detergent precursors. Although detergents produced from the 2-phenyl isomer may have about the same biodegradability, they often fall below the isomers in such quality standards as foaming ability, detergency and wettability.

It is therefore an objective of the invention to provide an improved process for the production of detergent alkylate by the reaction of olefinic hydrocarbons and aromatic hydrocarbons. It is another objective of the invention to reduce the amount of 2-phenyl isomers produced during the production of detergent alkylate from $C_6$ to $C_9$ aromatic hydrocarbons. It is a further objective of the invention to provide an improved process for the production of detergent alkylates from alpha-olefins.

The inventive concept comprises alkylating the aromatic hydrocarbon with the olefinic hydrocarbon in the presence of a surfactant. The tremendously large number of compounds which may be characterized as surfactants has prevented the development of a definitive characterization of this group of compounds. As used herein, the term "surfactant" is intended to indicate a compound which satisfies the six fundamental characteristics set out on page 507 of Volume 19 of *Kirk-Othmer Encyclopedia of Chemical Technology*, 2nd Edition, Interscience Publishers, 1969. These six fundamental characteristics include solubility in at least one phase of a liquid system, an amphipathic structure, the tendency to form oriented monolayers at phase interfaces, preferential equilibrium concentration at a phase interface as compared to the bulk of a solution, micelle formation, and the possession of some combination of the functional properties of surfactants, which include detergency, foaming, wetting, emulsifying, solubilizing and dispersing.

Preferably the surfactant is a hydrophilic or water liking compound. The preferred surfactant is a sulfonate, with alkylbenzene sulfonates being especially preferred. That is, the preferred surfactant is a detergent which may be produced from the detergent precursor formed in the subject alkylation process. A second class of surfactants which may be used in the subject process are the $C_{16}$ to $C_{19}$ organic acids which may be prepared by the addition of carbon monoxide and water to $C_{15}$ to $C_{18}$ linear olefins. These organic acids are often referred to as fatty acids. Other suitable surfactants include such anionic compounds as alkyl sulfates, aryl sulfates, paraffin sulfonates and olefin sulfonates. Alkyl and aryl polyethers, which are non-ionic surfactants, and alkyl or aryl quaternary ammonium halides may also be used as the surfactant.

The surfactant is intended to allow the intermediate carbonium ion in which the positive charge is initially found at the number 2 carbon atom to remain in existence for a longer length of time. This allows the carbonium ion to rearrange, with the charge transferring to a 3, 4, 5 or 6 position on the olefinic hydrocarbon. The result is a decrease in the production of the 2-phenyl isomer and a corresponding increase in other isomers.

It is preferred that the concentration of the surfactant in the reaction zone is below 0.1 wt.% based upon the total detergent alkylate product yield. It is also preferred that the surfactant is one which is preferentially soluble in the inorganic acid present in the reaction zone as the catalyst. That is, it is preferred that the surfactant is more soluble in the acid catalyst than in the hydrocarbons which are present in the reaction zone. The great majority of the surfactant will therefore remain in the liquid phase catalyst and will not be passed into the fractionation system utilized to recover the detergent alkylate. The consumption of the surfactant in the process will therefore be held to a minimum. However, the surfactant may if desired be one which is preferentially soluble in the hydrocarbons present in the reaction zone. Most of the surfactants will have a high molecular weight and correspondingly high boiling points which will prevent them going overhead in the fractionation columns usually employed to recover the detergent alkylate and aromatic hydrocarbons from the reaction zone effluent. The surfactant will therefore become concentrated in the bottoms stream removed from the detergent alkylate column, and a portion of this stream may therefore be recycled to the reaction zone.

The acid catalyst used in the subject process is preferably relatively anhydrous hydrofluoric acid (HF). Other acids such as sulfuric or phosphoric may be employed if desired. Most commercial processes for the production of detergent alkylate utilize two sequential contacting steps or reaction zones. The hydrofluoric acid used in the first reaction zone may be from about 85–95 wt.% HF and will typically be about 90 wt.% HF. The acid used in the next contacting step preferably contains more than 90 wt.% HF and is typically about 93-94 wt.% HF. The remainder of the acid phase is primarily made up of water and a small amount of relatively high boiling compounds referred to as acid-soluble oils.

The aromatic hydrocarbon which is consumed in the process is preferably high-purity substantially anhydrous benzene. The subject process may also be applied to the alkylation of other aromatic hydrocarbons having from 7 to about 9 carbon atoms per molecule including toluene, ethylbenzene, xylenes and phenol. The olefinic hydrocarbon fed to the reaction zone may contain from 7 to 20 or more carbon atoms per molecule. Preferably it is a straight-chain mono-olefin. More preferably, the olefinic hydrocarbon contains from about 10 to 15 carbon atoms per molecule. The use of an olefinic hydrocarbon other than an alpha-olefin is preferred since it should normally result in a better quality detergent alkylate. However, alpha-olefins may be utilized as the $C_7$ to $C_{20}$ mono-olefin, with the subject inventive concept showing the greatest relative improvement when alpha-olefins are consumed in the alkylation reaction.

The preferred method of producing the olefins which are charged to the reaction zone is by the dehydrogenation of the corresponding normal paraffins. The dehydrogenation zone in which this is accomplished may be integrated with the detergent alkylation process as described in U.S. Pat. Nos. 3,413,373; 3,484,498 and 3,494,971. The dehydrogenation reaction is not carried to completion and the effluent stream of the dehydrogenation zone is therefore a mixture of olefins and normal paraffins. To avoid the expense associated with separating this mixture of closely boiling compounds, the entire paraffin-olefin mixture is normally charged to the alkylation reaction zone. The paraffins pass through the alkylation zone substantially unaffected. They are recovered from the alkylation zone effluent stream by fractionation and then recycled to the dehydrogenation zone.

The alkylation zone is maintained at alkylation-promoting conditions. As used herein, the term "alkylation-promoting conditions" is intended to include a pressure sufficient to maintain the reactants and acid catalyst in a liquid phase. A general range of operating pressures for the alkylation zone is from about 2 to 41 atmospheres absolute. The temperature range covered by this set of conditions is from about $-20°$ C. to about 95° C., but the alkylation reaction is preferably conducted at a temperature of from 15° C. to 50° C. The volumetric ratio of acid catalyst to the total amount of hydrocarbons entering the first reaction zone should be maintained within the broad range of from about 0.2:1.0 to about 10:1. A preferred range for this ratio is from 1.0:1.0 to 2.5:1.0.

In order to reduce the production of polyalkylated benzene and to reduce the amount of olefin polymerization, the mole ratio of benzene or other aromatic hydrocarbon to the mono-olefin at the point of initial olefin-acid contact is maintained above 1.0:1.0, but preferably below 10.0:1.0. A range of typical commercial ratios is from about 3.0:1.0 to about 8.0:1.0.

Preferably, substantially all of the olefinic hydrocarbon is consumed in a first reaction zone under intense agitation. The effluent stream of this reaction zone comprises the excess aromatic hydrocarbon, the product alkylaromatic hydrocarbon, the surfactant, the acid catalyst, and any other hydrocarbon charged to the reaction zone, such as the previously referred to normal paraffins. This reaction zone effluent stream is preferably transferred to a first phase separation or settling zone. This separation zone is maintained under quiescent conditions effective to allow the separation of the denser inorganic acid catalyst from the less dense hydrocarbons. The acid catalyst is decanted from the bottom of the phase separation zone for recirculation. The hydrocarbon phase is removed from an upper portion of the phase separation zone and is normally passed into what is commonly referred to as a second reaction zone.

As essentially all of the olefinic hydrocarbon has been consumed in the first reaction zone, the second reaction zone is more properly thought of as a treatment zone utilized to produce a higher quality detergent alkylate. This treatment consists of the defluorination of the alkylate product of the first reaction zone and the extraction of naphthalenes and anthracenes. The second reaction zone or treatment zone may be operated in the same pressure range as the first reaction zone, but a higher temperature is preferred. This higher temperature should be at least 6-8 Centigrade degrees above that used in the first reaction zone. All temperatures specified herein are intended to refer to the average temperature maintained within the respective zone. The acid-catalyst ratio maintained in the second reaction zone will normally be slightly lower, and a typical ratio is about 1.0:1.0. The purity of acid used in the second step will, however, be higher. This is preferred because of the greater effectiveness of higher purity acid for the treatment of the alkylate. A higher purity acid is obtained by admixing newly regenerated acid into the alkylate-containing stream as it enters the second reaction zone.

The effluent stream of the second reaction zone is preferably passed into a second phase separation or settling zone. The denser acid phase which is removed from the bottom of this second settling zone is internally recycled for use in the first reaction zone. It contains a higher concentration of high molecular weight hydrocarbonaceous compounds referred to as tar or acid-soluble oils. The residence time of both the acid and the hydrocarbon phases in the phase separation zones should be in excess of 10 minutes but less than 30 minutes.

Those skilled in the art are familiar with the regeneration of the hydrofluoric acid used as a catalyst in the subject process. Information about the apparatus and conditions utilized for this operation is contained in the previously cited patents and also in U.S. Pat. Nos. 3,721,720 and 3,975,164. The regeneration operation is normally accomplished by stripping the acid under conditions sufficient to decompose alkylfluorides and to produce an overhead vapor stream containing HF and the stripping media. Benzene available within the process is a suitable stripping media. The overhead vapors of the stripping column are condensed to form an acid phase and a benzene phase containing dissolved hydrofluoric acid. The acid phase is withdrawn as the regenerated stream carried to the second reaction zone. The benzene phase may be charged to the first reaction zone in admixture with the other hydrocarbon streams fed to this zone.

The previously cited patents also describe fractionation systems and conditions suitable for use as an effective separation zone to recover the product detergent alkylate from the hydrocarbon stream removed from the first or the second phase separation zones. In one system for this separation, the effluent stream is passed into an upper portion of a first fractionation column which is operated under conditions effective for the stripping of hydrogen fluoride from the entering hydrocarbonaceous liquid. The resultant overhead stream of this column comprises hydrogen fluoride and some benzene which may be passed into the overhead system of the fractionation column used for the regeneration of the hydrogen fluoride catalyst. The bottoms stream of this HF stripper is passed into a second fractionation column referred to as a benzene column. This column is operated under conditions effective to cause the division of the entering hydrocarbons into a high-purity benzene stream which is removed as the overhead liquid and a bottoms stream containing the alkylate product. This bottoms stream is passed into a third fractionation column referred to as a paraffin column. Any non-reactive paraffins are removed in this column as a net overhead liquid stream.

The bottoms stream of the third fractionation column comprises the product alkylate, any surfactant charged to the first column and any higher molecular weight hydrocarbons formed by side reactions. This bottoms stream is passed into a fourth fractionation column which produces a high-purity overhead stream containing the detergent alkylate. A bottoms stream comprising polymerized olefins and polyalkylated aromatics is removed for disposal. This bottoms stream may also contain some of the surfactant charged to the reaction zone since the preferred surfactants will be relatively non-volatile substances. The third and the fourth fractionation columns are normally operated at a subatmospheric pressure. An alternative method of performing the recovery of the detergent alkylate is disclosed in U.S. Pat. No. 3,950,448.

I claim as my invention:

1. In a process for the production of detergent alkylate by the acid-catalyzed liquid-phase reaction of a $C_7$ to $C_{20}$ mono-olefin and benzene, resulting in a detergent alkylate having an objectionable 2-phenyl isomer content, the method of reducing said 2-phenyl isomer content of the alkylate which comprises performing said olefin-benzene reaction in the presence of a surfactant.

2. The method of claim 1 further characterized in that the acid catalyst is hydrofluoric acid.

3. The method of claim 2 further characterized in that the surfactant is an anionic surfactant selected from the group consisting of alkyl sulfates, aryl sulfates, paraffin sulfonates and olefin sulfonates.

4. The method of claim 1 further characterized in that the surfactant is an alkylbenzene sulfonate.

5. The method of claim 1 further characterized in that the surfactant is an acyclic $C_{16}$ to $C_{19}$ carboxylic acid.

* * * * *